US007074796B2

(12) United States Patent
Bang-Andersen et al.

(10) Patent No.: US 7,074,796 B2
(45) Date of Patent: Jul. 11, 2006

(54) 4-PHENYL-1-PIPERAZINYL, -PIPERIDINYL AND -TETRAHYDROPYRIDYL DERIVATIVES

(75) Inventors: Benny Bang-Andersen, Copenhagen N (DK); Jan Kehler, Kgs. Lyngby (DK); Jakob Felding, Charlottenlund (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 108 days.

(21) Appl. No.: 10/186,339

(22) Filed: Jun. 27, 2002

(65) Prior Publication Data
US 2003/0027832 A1    Feb. 6, 2003

Related U.S. Application Data

(63) Continuation of application No. PCT/DK00/00728, filed on Dec. 22, 2000.

(30) Foreign Application Priority Data
Dec. 30, 1999    (DK) ............................. 1999 01887

(51) Int. Cl.
A61K 31/496    (2006.01)
C07D 403/06    (2006.01)
(52) U.S. Cl. .................. 514/254.09; 544/373; 544/363; 544/392; 514/253.05; 514/253.06; 514/253.07; 514/255.03; 514/307; 514/311; 514/312; 514/323; 546/146; 546/150; 546/158; 546/168; 546/176; 546/201
(58) Field of Classification Search ................ 544/363, 544/368, 392, 373; 514/253.05, 253.06, 514/253.07, 254.09, 255.03
See application file for complete search history.

(56) References Cited
U.S. PATENT DOCUMENTS

| | | | | |
|---|---|---|---|---|
| 3,135,794 | A * | 6/1964 | Archer | 564/212 |
| 3,188,313 | A | 6/1965 | Archer | 260/268 |
| 3,468,882 | A | 9/1969 | Laskowski | 260/240 |
| 5,010,079 | A | 4/1991 | Manoury et al. | 514/253 |
| 5,418,237 | A | 5/1995 | Böttcher et al. | 514/253 |
| 5,556,857 | A * | 9/1996 | Oshiro et al. | 514/253.07 |
| 6,355,644 | B1 * | 3/2002 | Zhao et al. | 514/254.08 |

FOREIGN PATENT DOCUMENTS

| | | |
|---|---|---|
| EP | 0 354 094 B1 | 12/1991 |
| EP | 0 496 222 B1 | 1/1992 |
| FR | 1.551.082 | 12/1968 |
| WO | 94/24105 | 10/1994 |
| WO | 98/08816 | 3/1998 |
| WO | 99/09025 | 2/1999 |

OTHER PUBLICATIONS

CAS printout for Havera et al., Chem Abstract 73:109705.*
CAS printout for Archer et al., Chem Abstract 61:25461.*
CAS printout for Alter et al., Chem Abstract 60:45777.*
Jardemark et al. Dopamine D3 and D4 receptor antagonists in the treatment schizophrenia, Curr. Opin, Invest. Drugs, 3:101-105, 2002.*

(Continued)

Primary Examiner—Emily Bernhardt
(74) Attorney, Agent, or Firm—Darby & Darby

(57) ABSTRACT

The present invention relates to substituted 4-phenyl-1-piperazinyl derivatives having the formula I

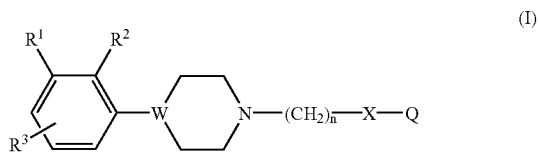

wherein W is C, CH or N, and the dotted line emanating from W indicates a bond when W is C and no bond when W is N or CH;
$R^1$ and $R^2$ are independently selected from hydrogen and halogen, provided at least one of $R^1$ and $R^2$ is a halogen atom;
$R^3$ is selected from hydrogen, halogen, $C_{1-6}$ alkyl, trifluoromethyl, $C_{1-6}$ alkoxy, aryloxy, aralkoxy, hydroxy, amino, $C_{1-6}$ alkylamino, di($C_{1-6}$ alkyl)amino, nitro and cyano
n is 2, 3, 4 or 5;
X is $CH_2$, O, S, CO, CS, SO or $SO_2$; and
Q is a group of formula

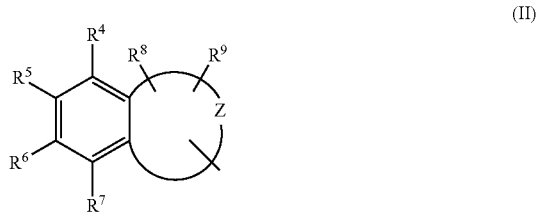

wherein Z is a chain of 3 to 4 chain members; wherein the chain members are selected from C, CH, $CH_2$, CO, N and NH, provided that only one of the chain members may be N or NH, and said chain optionally containing one or two double bonds; hvad med acyl??
$R^4$, $R^5$, $R^6$, $R^7$, $R^8$, $R^9$ and $R^{10}$ are independently selected from hydrogen, halogen, $C_{1-6}$ alkyl, trifluoromethyl, $C_{1-6}$ alkoxy, hydroxy, amino, $C_{1-6}$ alkylamino, di($C_{1-6}$ alkyl) amino nitro and cyano;
provided that X is not O or S when the group Q is attached via an N atom;
and any of its enantiomers and acid addition salts thereof.

These compounds have high affinity for $D_4$ receptors.

24 Claims, No Drawings

OTHER PUBLICATIONS

El-Gendy et al. Chemical Abstracts, vol. 117, No. 90076 (1992).*
Bourdais, Chemical Abstracts, vol. 78, No. 97706 (1973).*
Leurquin et al. Chemical Abstracts, vol. 76, No. 144827 (1972).*
Bourdais, Chemical Abstracts, vol. 74, No. 125324 (1971).*
Srinivas et al. Pharm.Pharmacol.Commun. vol. 5, p. 95-101 (1999).*
Zhao et al. Bioorganic & Medicinal Chemistry Letters, vol. 12, p. 3105-3109 (Nov. 2002).*
Mokrosz, M.J. et al., "5-$HT_{1A}$ and 5-$HT_{2A}$ receptor affinity and functional profile of some N-[3-(4-aryl-1-piperazinyl)propyl] derivatives of indolin-2(1H)-one, quinolin-2(1H)-one and isoquinolin-1 (2H)-one," *Pharmazie* 52, 1997, 6:432-428.
Böttcher, Henning et al., "Synthesis and Dopaminergic Activity of Some 3-(1,2,3,6-Tetrahydro-1-pyridylalkyl)indoles. A Novel Conformational Model to Explain Structure Activity Relationships," *J. Med. Chem.*, 1992, 35:4020-4026.
Misztal, Stanislaw et al., "Synthesis and Pharmacological Properties of N-Arylpiperazine-N'-Alkylindanes," *Pol. J. Pharmacol. Pharm.*, 1984, 36:697-703.

* cited by examiner

4-PHENYL-1-PIPERAZINYL, -PIPERIDINYL AND -TETRAHYDROPYRIDYL DERIVATIVES

FIELD OF THE INVENTION

This application is a continuation of International Application No. PCT/DK00/00728, filed Dec. 22, 2000. The prior application is hereby incorporated by reference in its entirety.

The present invention relates to a novel class of halogen substituted 4-phenyl-1-piperazinyl, -piperidinyl and -tetrahydropyridyl derivatives having affinity for dopamine $D_4$ receptors and $D_3$ receptors. The compounds of the invention are considered useful in the treatment of certain psychiatric and neurologic disorders, including psychosis.

BACKGROUND OF THE INVENTION

U.S. Pat. No. 3,188,313 relates to certain 1-(1-, 2-, and 3-indolylalkyl)piperazines, which are said to have CNS depressant and tranquillising effect.

Other compounds related to the compounds of the invention, which are said to interact with the dopamine and/or the serotonin system, are known in the art.

Thus, EP-B1-496 222, claims compounds having the formula

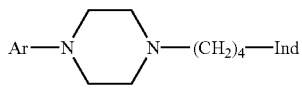

wherein Ar is a phenyl group, which may be substituted with halogen, alkyl, cyano, hydroxy etc. and Ind is 3-indolyl, which may be substituted with cyano, aminocarbonyl and aminocarbonylamino. The compounds disclosed in EP-B1-496 222 are said to be serotonine antagonists and agonists. It is also mentioned that the compounds have effect on dopamine accumulation in striatum and 5-HTP accumultation in N. Raphe. The compounds are said to be useful as anxiolytica, antidepressiva, neuroleptica and antihypertonica.

WO 99/09025 claims certain 2-(4-aryl-piperazin-1-yl)methyl-1H-indole derivatives. The compounds are said to be dopamine $D_4$ receptor agonists. Further, WO 94/24105 relates to 2-(2-(4-aryl-piperazin-1-yl)ethyl)-1H-indole derivatives, which are said to have selective affinity for the dopamine $D_4$ receptor subtype.

EP-B1-354 094 relates to certain oxindoles having the formula

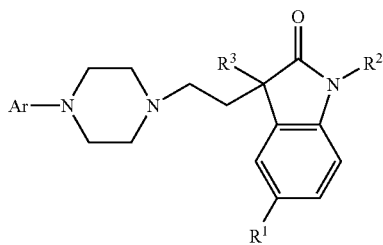

wherein $R^1$ is hydrogen, halogen or alkyl, $R^2$ is hydrogen or alkyl, $R^3$ is hydrogen, alkyl or —S-alkyl and Ar may be chlorophenyl and other substituted aryl groups. The compounds bind to the $5\text{-}HT_{1A}$ receptor and are said to be agonists, partial agonists or antagonists at this receptor. Certain of the compounds are said to possess activity at $5\text{-}HT_2$ receptors.

WO 98/08816 also describes oxindoles, which are said to be psychotropic drugs, and the application contains data showing the activity of certain of the compounds at the $D_4$ receptor.

Pharmazie, 1997, 52, 423–428 describes N-[3-(4-aryl-1-piperazinyl)alkyl] derivatives of indolin-2(1H)-one, quinolin-2(1H)-one and isoquinolin-1(2H)-one and their receptor affinities at the $5\text{-}HT_{1A}$ and the $5\text{-}HT_{2A}$ receptor. The compound 1-(3-(4-phenyl-1-piperazinyl)propyl)indolin-2(1H)-one is described as a $5\text{-}HT_{2A}$ antagonist with weak $5\text{-}HT_{1A}$ agonistic properties. The compound is suggested as a potential antidepressant and/or anxiolytic agent.

Subramanian et al., Heterocyclic Communications 1999, 5, 63–68 describes certain piperazinyl indolyl propanones claimed to show antagonism at dopamine $D_1/D_2$ receptors.

Further, Böttcher et al., J. Med. Chem. 1992, 35, 4020–4026, describes certain 3-(1,2,3,6-tetrahydro-1-pyridylalkyl)indoles having dopaminergic activity.

Finally, Pol. J. Pharmacol. Pharm. 1984, 36, 697–703 describes the compound 1-(3-(4-(3-chlorophenyl)-1-piperazinyl)propyl)indane as having serotinolytic properties.

Dopamine $D_4$ receptors belong to the dopamine $D_2$ subfamily of receptors, which is considered to be responsible for the antipsychotic effects of neuroleptics. The side effects of neuroleptic drugs, which primarily exert their effect via antagonism of $D_2$ receptors, are known to be due to $D_2$ receptor antagonism in the striatal regions of the brain. However, dopamine $D_4$ receptors are primarily located in areas of the brain other than striatum, suggesting that antagonists of the dopamine $D_4$ receptor will be devoid of extrapyramidal side effects. This is illustrated by the antipsychotic clozapine, which exerts higher affinity for $D_4$ than $D_2$ receptors, and is lacking extrapyramidal side effects (Van Tol et al. Nature 1991, 350, 610; Hadley Medicinal Research Reviews 1996, 16, 507–526 and Sanner Exp. Opin. Ther. Patents 1998, 8, 383–393).

A number of $D_4$ ligands, which were postulated to be selective $D_4$ receptor antagonists (L-745,879 and U-101958) have been shown to posses antipsychotic potential (Mansbach et al. Psychopharmacology 1998, 135, 194–200). However, recently it has been reported that these compounds are partial $D_4$ receptor agonists in various in vitro efficacy assays (Gazi et al. Br. J. Pharmacol. 1998, 124, 889–896 and Gazi et al. Br. J. Pharmacol. 1999, 128, 613–620). Furthermore, it was shown that clozapine, which is an effective antipsychotic, is a silent antagonist (Gazi et al. Br. J. Pharmacol. 1999, 128, 613–620).

Consequently, $D_4$ ligands, which are partial $D_4$ receptor agonists or antagonists, may have beneficial effects against psychoses.

Dopamine $D_4$ antagonists may also be useful for the treatment of cognitive deficits (Jentsch et al. Psychopharmacology 1999, 142, 78–84.

It has also been suggested that dopamine $D_4$ antagonists may be useful to reduce dyskinesia occurring as a result of the treatment of Parkinson's disease with L-dopa (Tahar et al. Eur. J. Pharmacol. 2000, 399, 183–186).

Dopamine $D_3$ receptors also belong to the dopamine $D_2$ subfamily of receptors, and they are preferentially located in limbic regions of the brain (Sokoloff et al. Nature 1990, 347, 146–151), such as the nucleus accumbens, where dopamine receptor blockade has been associated with antipsychotic activity (Willner *Int. Clinical Psychopharmacology* 1997, 12, 297–308). Furthermore, an elevation of the level of $D_3$ receptors in the limbic part of schizophrenic brains has been reported (Gurevich et al. *Arch. Gen. Psychiatry* 1997, 54, 225–32). Therefore, $D_3$ receptor antagonists may offer the potential for an effective antipsychotic therapy, free of the extrapyramidal side effects of the classical antipsychotic drugs, which primarily exert their effect by blockade of $D_2$ receptors' (Shafer et al. *Psychopharmacology* 1998, 135, 1–16; Schwartz et al. *Brain Research Reviews* 2000, 31, 277–287).

Moreover, $D_3$ receptor blockade results in a slight stimulation in the prefrontal cortex (Merchant et al. *Cerebral Cortex* 1996, 6, 561–570), which could be beneficial against negative, symptoms and cognitive deficits associated with schizophrenia. In addition, dopamine $D_3$ antagonists can reverse $D_2$ antagonist-induced EPS (Millan et al. *Eur. J. Pharmacol.* 1997, 321, R7–R9) and do not cause changes in prolactin (Reavill et al. *J. Pharmacol. Exp. Ther.* 2000, 294, 1154–1165). Consequently, $D_3$ antagonistic properties of an antipsychotic drug could reduce the negative symptoms and cognitive deficits and result in an improved side effect profile with respect to EPS and hormonal changes.

Dopamine $D_3$ agonists have also been considered relevant in the treatment of schizophrenia (Wustow et al. *Current Pharmaceutical Design* 1997, 3, 391–404).

According to the present invention, a novel class of dopamine $D_4$ receptor ligands is provided. Most of the compounds of the invention also have high affinity for the dopamine $D_3$ receptor and as mentioned above, dopamine $D_3$ antagonistic properties of an antipsychotic drug may reduce the negative symptoms and cognitive deficits of schizophrenia and result in an improved side effect profile.

Moreover, certain of the compounds of the invention have the further advantage of having only very weak effect at adrenergic alpha-1-receptors which imply a low propensity to cause orthostatic hypotension.

SUMMARY OF THE INVENTION

Accordingly, the present invention relates to the novel compounds of formula I

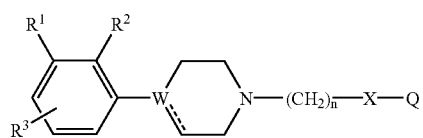

(I)

wherein W is C, CH or N and the dotted line emanating from W indicate a bond when W is C and no bond when W is CH or N;

$R^1$ and $R^2$ are independently selected from hydrogen and halogen provided that at least one of $R^1$ and $R^2$ is a halogen atom;

$R^3$ is selected from hydrogen, halogen, $C_{1-6}$-alkyl, $C_{2-6}$-alkenyl, $C_{2-6}$-alkynyl, trifluoromethyl, $C_{1-6}$-alkoxy, aryloxy, aralkoxy, hydroxy, amino, $C_{1-6}$-alkylamino, di($C_{1-6}$-alkyl)amino, nitro and cyano n is 2, 3, 4, or 5;

X is $CH_2$, O, S, CO, CS, SO or $SO_2$; and

Q is a group of formula

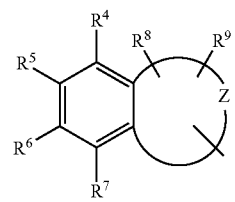

(II)

wherein Z is a chain of 3 to 4 chain members, wherein the chain members are selected from C, CH, $CH_2$, CO, N and NH, provided that only one of the chain members may be N or NH, said chain Z optionally containing one or two double bonds.

$R^4$, $R^5$, $R^6$, $R^7$, $R^8$ and $R^9$ are independently selected from hydrogen, halogen, trifluoromethyl, nitro, cyano, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, hydroxy, hydroxy-$C_{1-6}$ alkyl, amino, $C_{1-6}$-alkylamino, di($C_{1-6}$-alkyl)amino, acyl, aminocarbonyl, $C_{1-6}$-alkylaminocarbonyl and di($C_{1-6}$-alkyl)aminocarbonyl; provided that X is not O or S when the group Q is attached via an N atom;

and any of its enantiomers and acid addition salts thereof.

According to a preferred embodiment of the invention, R and R are both halogen, in particular chloro.

In another embodiment of the invention, one of $R^1$ and $R^2$ is halogen and the other is hydrogen. In particular, the invention relates to such compounds wherein $R^2$ is halogen and $R^1$ is hydrogen.

If $R^2$ is hydrogen and $R^1$ is chloro, Q is preferably selected from indolinyl, 1,2,3,4-tetrahydroisoquinolinyl, 1,2,3,4-tetrahydroquinolinyl or 1-indanyl.

In one particular embodiment of the invention, when $R^2$ is hydrogen and $R^1$ is halogen, $R^1$ is not chloro.

In a further embodiment of the invention, $R^1$ and $R^2$ are independently selected from hydrogen and chloro.

In another particular embodiment of the invention W is N.

In a preferred embodiment of the invention X is CO or $CH_2$.

In a further embodiment of the invention, Z is a chain of 3 to 4 chain members, wherein the chain members are selected from C, CH, $CH_2$, N and NH, provided that only one of the chain members may be N or NH.

Q may preferably be selected from optionally substituted 1-indolinyl, 3-indolyl, 1-indanyl, 2-oxo-1,2,3,4-tetrahydroquinolinyl and 1,2,3,4-tetrahydroisoquinolinyl.

In particular, Q is unsubstituted or substituted with halogen.

$R^3$ is preferably hydrogen or halogen and if $R^3$ is halogen it is preferably attached in the para position on the phenyl ring.

The compounds of the invention have been found to show high affinity for dopamine $D_4$ receptors and dopamine $D_3$ receptors, in certain cases combined with a very low effect at adrenergic alpha-1-receptors.

The compounds of the invention are therefore considered useful for the treatment of psychosis, including the positive and negative symptoms of schizophrenia.

Moreover, certain of the compounds have the further advantage of having only very weak effect at adrenergic alpha-1-receptors which imply a low propensity to cause orthostatic hypotension.

Some of the compounds interact with central serotonergic receptors, e.g. the 5-HT$_{1A}$ or 5-HT$_{2A}$ receptors and/or they act as 5-HT reuptake inhibitors.

These compounds of the invention may therefore also be useful for the treatment of disorders caused by imbalances in the serotonergic system including affective disorders such as generalised anxiety disorder, panic disorder, and obsessive compulsive disorder, depression and aggression.

In particular, compounds with combined effects at dopamine D$_4$ and 5-HT receptors and/or the 5-HT transporter may have the benefit of improved effect on other psychiatric symptoms associated with schizophrenia, such as depressive and anxiety symptoms.

Thus, in another aspect, the present invention provides a pharmaceutical composition comprising at least one compound of Formula I as defined above or a pharmaceutically acceptable acid addition salt thereof in combination with one or more pharmaceutically acceptable carriers or diluents.

The invention also relates to the use of a compound of the invention for the manufacture of a medicament useful in the treatment of psychosis including the positive and negative symptoms of schizophrenia, affective disorders such as generalised anxiety disorder, panic disorder, and obsessive compulsive disorder, depression, aggression, cognitive disorders and dyskinesia induced by treatment with L-dopa.

DETAILED DESCRIPTION OF THE INVENTION

Some of the compounds of general Formula I exist as optical isomers thereof and such optical isomers are also embraced by the invention.

The term C$_{1-6}$-alkyl refers to a branched or unbranched alkyl group having from one to six carbon atoms inclusive, such as methyl, ethyl, 1-propyl, 2-propyl, 1-butyl, 2-butyl, 2-methyl-2-propyl and 2-methyl-1-propyl. The terms C$_{1-6}$-alkoxy, C$_{1-6}$-alkylthio, C$_{1-6}$-alkylamino, di(C$_{1-6}$-alkyl)amino etc. designate such groups in which the alkyl group is C$_{1-6}$-alkyl as defined above.

The term aryl refers to a carbocyclic aromatic group, such as phenyl, naphthyl, in particular phenyl, including methyl substituted naphthyl, or phenyl.

The term aralkyl means aryl-C$_{1-6}$-alkyl, wherein aryl and C$_{1-6}$-alkyl is as defined above.

The terms aralkoxy and aryloxy means aryl-C$_{1-6}$alkyl—O— and aryl—O— where aryl and C$_{1-6}$-alkyl are as defined above.

Halogen means fluoro, chloro, bromo or iodo. A group Q wherein Z is as defined above includes groups such as:

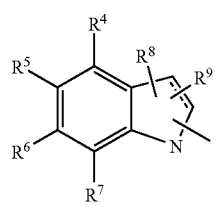

(IIa)

-continued

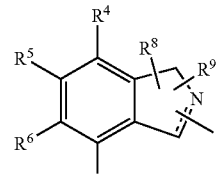

(IIb)

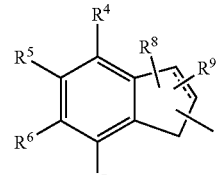

(IIc)

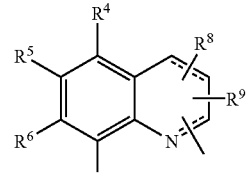

(IId)

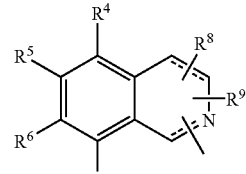

(IIe)

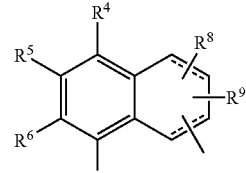

(IIf)

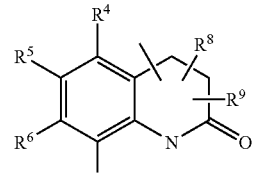

(IIg)

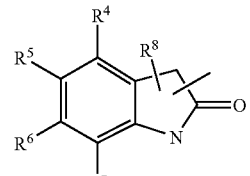

(IIh)

wherein R$^4$–R$^9$ are as defined above and the dotted line indicates an optional bond.

Preferred compounds of the invention are the compounds selected from

3-[4-(2,3-Dichlorophenyl)piperazin-1-yl]-1-(2,3-dihydro-1H-indol-1-yl)propan-1-one, 4-[4-(2,3-Dichlorophenyl)piperazin-1-yl]-1-(2,3-dihydro-1H-indol-1-yl)butan-1-one,
5-[4-(2,3-Dichlorophenyl)piperazin-1-yl]-1-(2,3-dihydro-1H-indol-1-yl)pentan-1-one,
4-[4-(2-Chlorophenyl)piperazin-1-yl]-1-(2,3-dihydro-1H-indol-1-yl)butan-1-one,
4-[4-(3-Chlorophenyl)piperazin-1-yl]-1-(2,3-dihydro-1H-indol-1-yl)butan-1-one,
1-{3-[4-(2,3-Dichlorophenyl)piperazin-1-yl]propyl}-2,3-dihydro-1H-indole,
1-{4-[4-(2,3-Dichlorophenyl)piperazin-1-yl]butyl}-2,3-dihydro-1H-indole,
1-{5-[4-(2,3-Dichlorophenyl)piperazin-1-yl]pentyl}-2,3-dihydro-1H-indole,
1-{4-[4-(2-Chlorophenyl)piperazin-1-yl]butyl}-2,3-dihydro-1H-indole,
1-{4-[4-(3-Chlorophenyl)piperazin-1-yl]butyl}-2,3-dihydro-1H-indole,
1-(2,3-Dichlorophenyl)-4-[4-(indan-1-yl)butyl]piperazine,
6-Chloro-3-{2-[4-(2,3-dichlorophenyl)piperazin-1-yl]ethylsulfanyl}-1H-indole,
3-{3-[4-(2,3-Dichlorophenyl)piperazin-1-yl]propyl}-1H-indole,
3-{4-[4-(2,3-Dichlorophenyl)piperazin-1-yl]butyl}-1H-indole,
3-{3-[4-(2,3-Dichlorophenyl)piperazin-1-yl]propyl}-5-fluoro-1H-indole,
3-{4-[4-(2,3-Dichlorophenyl)piperazin-1-yl]butyl}-5-fluoro-1H-indole,
6-Chloro-3-{3-[4-(2,3-dichlorophenyl)piperazin-1-yl]propyl}-1H-indole,
1-{4-[4-(2,3-Dichlorophenyl)piperazin-1-yl]butyl}-3,4-dihydroquinolin-2(1H)-one,
3-[4-(2,3-Dichlorophenyl)piperazin-1-yl]-1-(5-fluoro-2,3-dihydro-1H-indol-1-yl)propan-1-one,
4-[4-(2,3-Dichlorophenyl)piperazin-1-yl]-1-(5-fluoro-2,3-dihydro-1H-indol-1-yl)butan-1-one,
5-[4-(2,3-Dichlorophenyl)piperazin-1-yl]-1-(5-fluoro-2,3-dihydro-1H-indol-1-yl)pentan-1-one,
3-[4-(2,3-Dichlorophenyl)piperazin-1-yl]-1-(3,4-dihydro-1H-isoquinolin-2-yl)-propan-1-one,
4-[4-(2,3-Dichlorophenyl)piperazin-1-yl]-1-(3,4-dihydro-1H-isoquinolin-2-yl)-butan-1-one,
5-[4-(2,3-Dichloro-phenyl)-piperazin-1-yl]-1-(3,4-dihydro-1H-isoquinolin-2-yl)-pentan-1-one,
3-[4-(2-Chlorophenyl)piperazin-1-yl]-1-(2,3-dihydro-1H-indol-1-yl)propan-1-one,
5-[4-(2-Chlorophenyl)piperazin-1-yl]-1-(2,3-dihydro-1H-indol-1-yl)pentan-1-one,
3-[4-(3-Chlorophenyl)piperazin-1-yl]-1-(2,3-dihydro-1H-indol-1-yl)propan-1-one,
5-[4-(3-Chlorophenyl)piperazin-1-yl]-1-(2,3-dihydro-1H-indol-1-yl)pentan-1-one,
3-[4-(3-Chlorophenyl)piperazin-1-yl]-1-(5-fluoro-2,3-dihydro-1H-indol-1-yl)propan-1-one,
5-[4-(3-Chlorophenyl)piperazin-1-yl]-1-(5-fluoro-2,3-dihydro-1H-indol-1-yl)pentan-1-one,
3-[4-(2-Chlorophenyl)piperazin-1-yl]-1-(5-fluoro-2,3-dihydro-1H-indol-1-yl)propan-1-one,
4-[4-(2-Chlorophenyl)piperazin-1-yl]-1-(5-fluoro-2,3-dihydro-1H-indol-1-yl)butan-1-one,
3-[4-(3-Chlorophenyl)piperazin-1-yl]-1-(3,4-dihydro-1H-isoquinolin-2-yl)-propan-1-one,
5-[4-(3-Chlorophenyl)piperazin-1-yl]-1-(3,4-dihydro-1H-isoquinolin-2-yl)-pentan-1-one,
3-[4-(2-Chlorophenyl)piperazin-1-yl]-1-(3,4-dihydro-1H-isoquinolin-2-yl)-propan-1-one,
4-[4-(2-Chlorophenyl)piperazin-1-yl]-1-(3,4-dihydro-1H-isoquinolin-2-yl)-butan-1-one,
1-(2,3-Dihydro-1H-indol-1-yl)-3-[4-(2-fluoro-phenyl)-piperazin-1-yl]-propan-1-one,
1-(2,3-Dihydro-1H-indol-1-yl)-4-[4-(2-fluoro-phenyl)-piperazin-1-yl]-butan-1-one,
1-(2,3-Dihydro-1H-indol-1-yl)-5-[4-(2-fluoro-phenyl)-piperazin-1-yl]-pentan-1-one,
1-(5-Fluoro-2,3-dihydro-1H-indol-1-yl)-3-[4-(2-fluoro-phenyl)-piperazin-1-yl]-propan-1-one,
1-(5-Fluoro-2,3-dihydro-1H-indol-1-yl)-4-[4-(2-fluoro-phenyl)-piperazin-1-yl]-butan-1-one,
1-(5-Fluoro-2,3-dihydro-1H-indol-1-yl)-5-[4-(2-fluoro-phenyl)-piperazin-1-yl]-pentan-1-one,
3-[4-(2,4-Difluoro-phenyl)-piperazin-1-yl]-1-(2,3-dihydro-1H-indol-1-yl)propan-1-one,
4-[4-(2,4-Difluoro-phenyl)-piperazin-1-yl]-1-(2,3-dihydro-1H-indol-1-yl)butan-1-one, and
5-[4-(2,4-Difluoro-phenyl)-piperazin-1-yl]-1-(2,3-dihydro-1H-indol-1-yl)pentan-1-one and pharmaceutically acceptable acid addition salts thereof.

The acid addition salts of the compounds of the invention may be pharmaceutically acceptable salts formed with non-toxic acids. Exemplary of such organic salts are those with maleic, fumaric, benzoic, ascorbic, succinic, oxalic, bis-methylenesalicylic, methanesulfonic, ethanedisulfonic, acetic, spropionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The compounds of the invention may be prepared as follows:

a) Reducing the carbonyl group of a compound of formula III

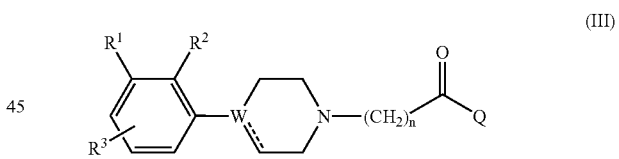

wherein $R^1$, $R^2$, $R^3$, W, n, Q and the dotted line are as previously defined;

b) alkylating an amine of formula IV with a reagent of formula V

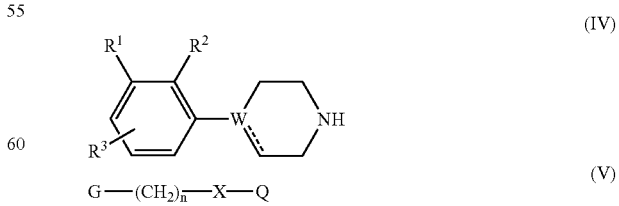

wherein $R^1$, $R^2$, $R^3$, X, W, n, Q and the dotted line are as previously defined, and G is a suitable leaving group such as halogen, mesylate or tosylate;

c) reductive alkylation of an amine of the formula IV with a reagent of formula VII

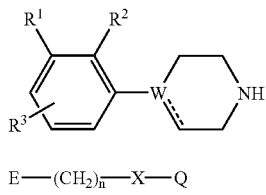

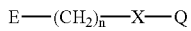

wherein $R^1$, $R^2$, $R^3$, X, n, W, Q and the dotted line are as previously defined, and E is either an aldehyde or an activated carboxylic acid group;

d) reducing the amide group of a compound of formula VIII

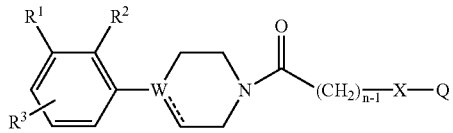

wherein $R^1$, $R^2$, $R^3$, X, n, W, Q and the dotted line are as previously defined;

e) acylation or reductive alkylation of an amine of the formula II'

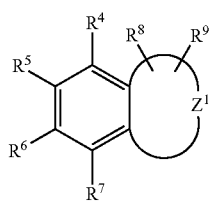

wherein $Z^1$ is a chain of 3 to 4 chain members, wherein the chain members are selected from C, CH, $CH_2$, CO and NH, provided that one of the chain members is NH, and said chain optionally containing one or two double bonds, with a reagent of formula IX

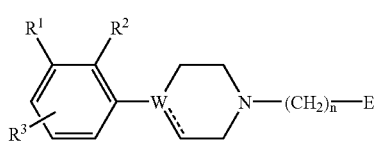

wherein $R^1$, $R^2$, $R^3$, n, W and the dotted line are as previously defined, and E is either an aldehyde or an activated carboxylic acid group f) Lewis-acid catalyzed cleavage of a resin-bound ester of formula X by an amine of the formula Q'

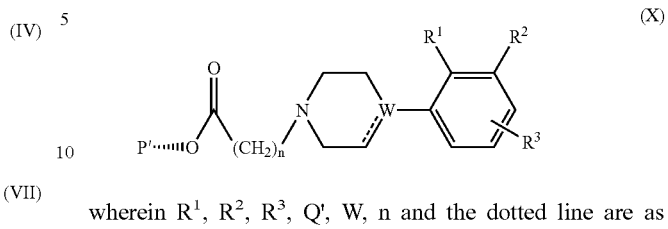

wherein $R^1$, $R^2$, $R^3$, Q', W, n and the dotted line are as previously defined, or g) reduction of the double bond in a compound of formula XI

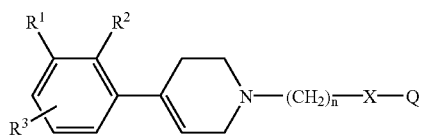

wherein $R^1$, $R^2$, $R^3$, n, X and Q are as previously defined, whereupon the compound of formula I is isolated as the free base or an acid addition salt thereof.

The reduction according to method a) is preferably carried out in an inert organic solvent such as diethyl ether or tetrahydrofuran in the presence of alane or lithium aluminium hydride from 0° C. to reflux temperature. Method b) may be used to prepare starting materials of formula III.

The alkylation according to method b) is conveniently performed in an inert organic solvent such as a suitably boiling alcohol or ketone, preferably in the presence of an organic or inorganic base (potassium carbonate, diisopropylethylamine or triethylamine) at reflux temperature. Alternatively, the alkylation can be performed at a fixed temperature, which is different from the boiling point, in one of the above-mentioned solvents or in dimethyl formamide (DMF), dimethylsulfoxide (DMSO) or N-methylpyrrolidin-2-one (NMP), preferably in the presence of a base.

Amines of formula IV are either commercially available or known from the literature (e.g. Oshiro et al. *J. Med. Chem.* 1991, 34, 2014–2023, Oshiro et al. *J. Med. Chem.* 1998, 41, 658–667, and Oshiro et al. *J. Med. Chem.* 2000, 43, 177–189). Alkylating reagents of formula V are known from the literature, or they can be prepared by methods obvious to a chemist skilled in the art by an analogous synthetic sequence. Thus, key intermediates such as halo-(2,3-dihydro-1H-indol-1-yl)alkan-1-one are prepared by addition of a haloalkanoyl chloride to a 2,3-dihydro-1H-indole in the presence of base. Similarly, halo-(3,4-dihydro-1H-isoquinolin-2-yl)alkan-1-one may be prepared from a haloalkanoyl chloride and a 3,4-dihydro-1H-isoquinoline. The 2,3-dihydro-1H-indoles are either commercially available or prepared from the corresponding 1H-indoles by reduction of the 1H-indole with e.g. sodium cyanoborohydride in acetic acid or in trifluoroacetic acid whereas the 3,4-dihydro-1H-isoquinolines are commercially available or described in the literature. Alkylating haloalkyl-1H-indoles were prepared by literature methods (Benghiat et al. *J. Med. Chem.* 1983, 26, 1470–1477) or analogous to methods described in the literature (Brodfuehrer et al. *J. Org. Chem.* 1997, 62, 9192 and WO 00/35872). Alkylating 3-haloalkylindanes or other types of alkylating alkylindanes can be prepared from known indanylalkancarboxylic acids (Mukhopadhyay et al. *J. Indian Chem. Soc.* 1985, 62, 690–692 and Tanaka et al. *J. Med. Chem.* 1994, 37, 2071–2078) by well known procedures. Alkylating 1-(haloalkyl)-3,4-dihydroquinolin-2(1H)-one can be prepared as described in EP-B 1-512525.

The reductive alkylation according to methods c) and e) can be performed in two steps, e.g. coupling of amines of formula VI/II' with reagent of formula VII/IX by standard methods via the carboxylic acid chloride, activated esters or by use of carboxylic acids in combination with coupling reagents such as e.g. dicyclohexyl carbodiimide followed by reduction of the resulting amide with lithium aluminium hydride or alane. The reaction can also be performed by a standard one-pot procedure, e.g. by the use of reductive amination of amines of formula VI/II' with aldehydes of formula VII/IX. Carboxylic acids or aldehydes of formula VII are either commercially available or described in the literature. Thus, key intermediates have been described in the literature such as indanylalkancarboxylic acids (Mukhopadhyay et al. *J. Indian Chem. Soc.* 1985, 62, 690–692 and Tanaka et al. *J. Med. Chem.* 1994, 37, 2071–2078), substituted 3-(1H-indol-3-yl)propionic acids (Carbonnelle et al. *Tetrahedron* 1998, 39, 4471–4472) and (2,3-dihydro-1H-indol)alkancarboxylic acids (WO 98/28293 and Ly et al. *Tetrahedron Letts.* 1999, 40, 2533–2536). Other substituted (TH-indol-3-yl)alkancarboxylic acids can be prepared by chain elongation of readily accessible 3-indoleglyoxylyl chlorides (Speeter et al. *J. Am. Chem. Soc.* 1954, 76, 6208–6210 and Nichols et al. *Synthesis* 1999, 6, 935–938). The 3-indoleglyoxylyl chlorides may be prepared from commercially available 1H-indoles. Various substituted (1H-indol-3-ylsulfanyl)alkancarboxylic acids can be prepared in an analogous manner as described for aminoalkylsulfanyl-1H-indoles (Zelesko et al. *J. Med. Chem.* 1983, 26, 230–237 or WO 91/04973) by in situ alkylation of substituted sodium 3-indolylthiolate with alkyl haloalkanoates and subsequent hydrolysis of the ester group.

Reduction of amide groups according to method d) is most conveniently performed with lithium aluminium hydride or alane in an inert organic solvent such as e.g. tetrahydrofuran or diethylether from 0° C. to reflux temperature.

Acylation according to method e) can be performed by standard literature methods, e.g. coupling of amines of formula Q' with reagent of formula IX by standard methods via the carboxylic acid chloride, activated esters or by use of carboxylic acids in combination with coupling reagents such as e.g. dicyclohexyl carbodiimide.

The Lewis acid catalyzed conversion of an ester to an amide according to method f) can be performed by standard literature methods (Barn et al. *Tet. Lett.* 1996, 37, 3213–3216). The Resin bound ester X can likewise be synthesised according to the literature (see e.g. Barn et al. *Tet. Lett.* 1996, 37, 3213–3216).

The reduction of the double bond according to method g) is generally performed by catalytic hydrogenation at low pressure (<3 atm.) in a Parr apparatus, or by using reducing agents such as diborane or hydroboric derivatives as produced in situ from $NaBH_4$ in trifluoroacetic acid in inert solvents such as tetrahydrofuran (TIF), dioxane, or diethyl ether.

Experimental Section

Melting points were determined on a Buchi B-535 apparatus and are uncorrected. Mass spectra were obtained on a Quattro MS-MS system from VG Biotech, Fisons Instruments or on a Sciex API 150EX from Perkin Elmer. Spectra were obtained at two sets of operating conditions by the use of either electrospray ionisation or ACPI: one set to obtain molecular weight information and the other set to induce fragmentation patterns. $^1H$ NMR spectra were recorded at 250.13 MHz on a Bruker AC 250 or at 500.13 MHz on a Bruker DRX 500. Deuterated chloroform (99.8% D) or dimethylsulfoxide (99.9% D) were used as solvents. TMS was used as internal reference standard. Chemical shifts are expressed as ppm values. The following abbreviations are used for multiplicity of NMR signals: s=singlet, d=doublet, t=triplet, q=quartet, qv=quintet, h=heptet, dd=double doublet, dt=double triplet, dq=double quartet, tt=triplet of triplets, m=multiplet, b=broad. NMR signals corresponding to acidic protons are to some extent omitted. Content of water in crystalline compounds were determined by Karl Fischer titration. For column chromatography silica gel of type Kieselgel 60, 40-60 mesh ASTM was used.

Preparation of Intermediates

A. Alkylating Reagents

3-Chloro-1-(2,3-dihydro-1H-indol-1-yl)propan-1-one

A mixture of 2,3-dihydro-1H-indole (50 g), triethylamine (132 g) and tetrahydrofuran (1000 mL) was cooled down to 10° C. followed by the addition (over a period of 60 min) of a solution of 3-chloropropanoyl chloride (55 g) in tetrahydrofuran (400 mL). The mixture was filtered, and the remaining solution was evaporated in vacuo to dryness. The residue was purified by flash chromatography (eluent:ethyl acetate/heptane 1:3) giving the title compound as a crystalline white material (31 g).

The following compounds were prepared in a similar manner

4-Chloro-1-(2,3-dihydro-1H-indol-1-yl)butan-1-one from 2,3-dihydro-1H-indole and 4-chlorobutanoyl chloride 5-Bromo-1-(2,3-dihydro-1H-indol-1-yl)pentan-1-one from 2,3-dihydro-1H-indole and 5-bromopentanoyl chloride The following two compounds were prepared as described in Benghiat et al. *J. Med. Chem.* 1983, 26, 1470–1477

3-(3-Bromopropyl)-1H-indole 3-(4-Bromobutyl)-1H-indole 3-(3-Chloropropyl)-5-fluoro-1H-indole The compound 5-chloropentan-1-ol (16.2 mL) was dissolved in cold 5 mM 2,2,6,6-tetramethylpiperidine-1-yloxy (tempo) in dichloromethane (240 mL) and cooled down to 0° C. with an ice bath. Potassium bromide (0.5 M in water, 24 mL) was added, and this was followed by the addition (in one portion at 5° C. under vigorous stirring) of a solution of sodium hydrogencarbonate (24 g) in aqueous sodium hypochlorite (0.3 M, 500 mL). The resulting mixture was stirred at 5° C. for 20 min, and the phases were separated. The water phase was extracted with dichloromethane (200 mL), and the combined organic phases were evaporated in vacuo giving 5-chloropentanal as a clear oil (16 g). Subsequently, 5-chloropentanal was suspended in water (100 mL) followed by addition of 4-fluorophenylhydrazine hydrochloride (19.5 g) and toluene (800 mL), and the mixture was stirred at room temperature for 15 min. Phosphoric acid (85%, 100 mL) was added and the mixture was boiled under reflux for 2 h. The mixture was cooled to room temperature and the phases were separated. The organic phase was washed with saturated aqueous sodium hydrogencarbonate, dried ($MgSO_4$) and evaporated in vacuo to yield an orange oil. The crude product was purified by flash chromatography on silicagel (eluent:ethylacetate/heptane 1:4) to give the title compound as an orange oil (14 g).

The following compound was prepared in a similar manner 3-(4-Chlorobutyl)-5-fluoro-1H-indole from 6-chlorohexan-1-ol and 4-fluorophenylhydrazine hydrochloride 6-Chloro 3-(3-iodopropyl)-1H-indole The alcohol 2-(6-chloro-1H-indol-3-yl)ethanol (25 g, prepared analogous to compounds described in Demerson et al. *J. Med. Chem.* 1976, 19, 391–395 from 6-chloro-1H-indole and oxalyl chloride) was dissolved in tetrahydrofuran (300 mL) followed by the addition of triethylamine (17.7 mL). The resulting mixture was cooled to 5–6° C. followed by the addition of a solution of methanesulfonic acid chloride (14.6 g) in tetrahydrofuran (100 mL). The mixture was stirred at room temperature for 2 h, filtered and evaporated to dryness in vacuo. The residue was dissolved in acetone followed by addition of sodium iodide (96.2 g), and the resulting mixture was boiled under reflux for 4 h. The mixture was poured onto brine and the aqueous phase was extracted with ethyl acetate. The combined organic phases were dried ($MgSO_4$), filtered and concentrated in vacuo (38.2 g). The residue (30 g) was dissolved in dimethylsulfoxide (DMSO, 200 mL) and added drop-wise to a suspension of NaCN (15 g) and DMSO (250 mL) at 80° C. The resulting mixture was stirred at 100° C. for 1 h, cooled down to room temperature and poured onto brine. The aqueous phase was extracted with diethyl ether, and the combined organic phase was dried ($MgSO_4$), filtered and concentrated in vacuo to yield crude intermediate (22.5 g). The residue was dissolved in methanol (750 mL) and added a mixture of HCl/methanol resulting in a combined solution of about 1 M HCl in methanol. The mixture was stirred at room temperature for 24 h followed by heating at 40° C. for an additional 3 h. The solvent was removed in vacuo, and the residue was dissolved in a mixture of diethyl ether and water. The resulting mixture was stirred at room temperature for 30 min. and the phases were separated. The aqueous phase was extracted an additional two times with diethyl ether and the combined organic phase was washed with brine, dried ($MgSO_4$), filtered and concentrated in vacuo (18.2 g). The residue was dissolved in tetrahydrofuran (300 mL) and added drop-wise to a suspension of $LiAlH_4$ (11.6 g) in tetrahydrofuran (1000 mL). The resulting mixture was boiled under reflux for 3 h, cooled down to 10° C. and worked up by the use of an equivalent amount of water. The organic phase was dried ($MgSO_4$), filtered and concentrated in vacuo (16.6 g). The residue (8 g) was dissolved in tetrahydrofuran (100 mL) and triethylamine (3.9 g) and cooled down to 10° C. followed by the addition of a solution of methanesulfonic acid chloride (4.4 g) in tetrahydrofuran (50 mL). The mixture was stirred at room temperature for 2 h and then evaporated to dryness in vacuo. The residue was dissolved in acetone followed by the addition of NaI (28.6 g), and the resulting mixture was boiled under reflux for 3 h. The mixture was poured onto brine, and the aqueous phase was extracted with tetrahydrofuran. The combined organic phase was dried ($MgSO_4$), filtered and concentrated in vacuo (17.4 g).

The following compound was prepared in a similar manner 4-(Indan-1-yl)butyl Methanesulfonate from 4-(indan-1-yl)butanoic acid prepared as described by Mukhopadhyay et al. *J. Indian Chem. Soc.* 1985, 62, 690–692.

1-(4-Bromobutyl)-3,4-dihydroquinolin-2(1H)-one

A suspension of sodium hydride (6.8 g, 60% dispersion in mineral oil) and dimethyl formamide (200 mL) was kept at 20–30° C. followed by the addition of a solution of 3,4-dihydroquinolin-2(1H)-one (25 g) in dimethyl formamide (100 mL). The resulting mixture was stirred at room temperature for 30 min followed by the addition of a solution of 1,4-dibromobutane (184 g) in dimethyl formamide (200 mL) at a temperature of 20–40° C. The reaction mixture was stirred at room temperature for 30 min and evaporated in vacuo. The remaining oil was poured into ice water and extracted with ethyl acetate. The combined organic phases were washed with water and brine, treated with charcoal, dried ($MgSO_4$) and evaporated in vacuo. The remaining oil was purified by flash chromatography (eluent:ethyl acetate/heptane 1:1) giving the title compound as a red oil (36 g).

B. Acylating Reagents (6-Chloro-1H-indol-3-ylsulfanyl)acetic Acid

The compounds 6-chloro-1H-indole (15.1 g) and thiourea (7.6 g) were dissolved in methanol (150 mL) followed by the addition of a solution of iodine/potassium iodide (1 M, 100 mL) under stirring. The solution was stirred at room temperature for 2 h and then evaporated in vacuo to give an oil. Sodium hydroxide (1.5 M, 200 mL) was added, and the solution was heated at 90° C. for 90 min. This solution was cooled to room temperature and extracted with diethyl ether (discarded). The aqueous phase was added diethyl ether (100 mL) and ethyl chloroacetate (10 mL), and the resulting mixture was stirred at room temperature for 16 h. The phases were separated, and the aqueous phase was extracted with diethyl ether. The combined organic phases were collected and dried ($MgSO_4$). The suspension was filtered, and the organic phase was evaporated to dryness to give a brown oil (18.1 g). The oil was dissolved in ethanol (50 mL) followed by the addition of a solution of water (50 mL) and potassium hydroxide (4.0 g). The resulting mixture was boiled under reflux for 2 h and cooled to room temperature. The pH of the mixture was adjusted to 3–4 by the addition of hydrochloride acid (1 M). Water was added (100 mL), and the aqueous phase was extracted with ethyl acetate. The combined organic phases were dried ($MgSO_4$), filtered and evaporated in vacuo to give the title compound as an oil (12.3 g).

Preparation of the Compounds of the Invention

EXAMPLE 1

1a, 3-[4-(2,3-Dichlorophenyl)piperazin-1-yl]-1-(2,3-dihydro-1H-indol-1-yl)propan-1-one A mixture of 1-(2,3-dichlorophenyl)piperazine, hydrochloride (8.0 g) and potassium carbonate (15 g) in a mixture of butanone (50 mL) and dimethyl formamide (5 mL) was heated to 50° C. followed by the addition of 3-chloro-1-(2,3-dihydro-1H-indol-1-yl)propan-1-one (6.0 g). The resulting mixture was boiled under reflux for 40 h and filtered hot. The remaining organic phase was left to crystallise, and a white crystalline material was collected by filtration and washed with acetone (8.5 g). Mp 157–158° C. $^1$H NMR (DMSO-$d_6$): 2.60 (s, 4H); 2.60–2.80 (m, 4H); 3.00 (s, 4H);

3.15 (t, 2H); 4.10 (t, 2H); 6.95 (t, 1H); 7.10–7–15 (m, 2H); 7.20 (d, 1H); 7.25–7.35 (m, 2H); 8.10 (d, 1H). MS m/z: 404 (MH+), 243.

1b, 4-[4-(2,3-Dichlorophenyl)piperazin-1-yl]-1-(2,3-dihydro-1H-indol-1-yl)butan-1-one A mixture of 1-(2,3-dichlorophenyl)piperazine, hydrochloride (8.0 g) and diisopropylethylamine (10 mL) in dimethyl formamide (50 mL) was heated to 45° C. followed by the addition of 4-chloro-1-(2,3-dihydro-1H-indol-1-yl)butan-1-one (6.7 g). The resulting mixture was heated at 100° C. for 6 h, cooled to room temperature and poured into water. The aqueous phase was extracted with diethyl ether, and the combined organic phases were dried (MgSO$_4$), filtered and evaporated in vacuo to give a black oil (14.2 g). The oil was crystallised from acetone, and the formed crystals were recrystallised from ethanol to give a white crystalline material (3.8 g). Mp 134–136° C. $^1$H NMR (CDCl$_3$): 1.90–2.05 (m, 2H); 2.45–2.60 (m, 4H); 2.65 (s, 4H); 3.00 (s, 4H); 3.20 (t, 2H); 4.10 (t, 2H); 6.90 (d, 1H); 7.00 (t, 1H); 7.05–7–25 (m, 4H); 8.25 (d, 1H). MS m/z: 418 (MH+), 299, 228, 188.

1c. 5-[4-(2,3-Dichlorophenyl)piperazin-1-yl]-1-(2,3-dihydro-1H-indol-1-yl)pentan-1-one A mixture of 1-(2,3-dichlorophenyl)piperazine hydrochloride (8.0 g) and diisopropylethylamine (15 mL) in butanone (50 mL) was heated to 45° C. followed by the addition of 5-bromo-1-(2,3-dihydro-1H-indol-1-yl)pentan-1-one (5.4 g). The resulting mixture was boiled under reflux for 40 h and filtered hot. The remaining organic phase was left to crystallise, and a white crystalline material was collected by filtration and washed with acetone (3.8 g). Mp 121–123° C. $^1$H NMR (DMSO-d$_6$): 1.50–1.70 (m, 4H); 2.30–2.65 (m, 8H); 3.00 (s, 4H); 3.15 (t, 2H); 4.10 (t, 2H); 6.95 (t, 1H); 7.10–7–15 (m, 2H); 7.20 (d, 1H); 7.25–7.35 (m, 2H); 8.10 (d, 1H). MS m/z: 432 (MH+), 315, 202.

The following compounds were prepared in a similar manner 1d, 4-[4-(2-Chlorophenyl)piperazin-1-yl]-1-(2,3-dihydro-1H-indol-1-yl)butan-1-one from 1-(2-chlorophenyl)piperazine, hydrochloride and 4-chloro-1-(2,3-dihydro-1H-indol-1-yl)butan-1-one. Mp 119–121° C. $^1$H NMR (DMSO-d$_6$): 1.75–1.85 (m, 2H); 2.35–2.50 (m, 4H); 2.55 (s, 4H); 3.95 (s, 4H); 3.15 (t, 2H); 4.10 (t, 2H); 6.95 (t, 1H); 7.05 (t, 1H); 7.10 (d, 1H); 7.15 (t, 1H); 7.20 (d, 1H); 7.25 (t, 1H); 7.40 (d, 1H); 8.10 (d, 1H). MS m/z: 384 (MH+), 265, 188.

1e, 4-[4-(3-Chlorophenyl)piperazin-1-yl]-1-(2,3-dihydro-1H-indol-1-yl)butan-1-one from 1-(3-chlorophenyl)piperazine, dihydrochloride and 4-chloro-1-(2,3-dihydro-1H-indol-1-yl)butan-1-one. Mp 102–107° C. $^1$H NMR (DMSO-d$_6$): 1.75–1.85 (m, 2H); 2.35 (t, 2H); 2.45–2.55 (m, 6H); 3.10–3.20 (m, 6H); 4.10 (t, 2H); 6.75 (d, 1H); 6.85 (d, 1H); 6.90 (s, 1H); 6.95 (t, 1H); 7.10 (t, 1H); 7.15–7.25 (m, 2H); 8.10 (d, 1H). MS m/z: 384 (MH+), 265, 188.

EXAMPLE 2

2a, 1-{3-[4-(2,3-Dichlorophenyl)piperazin-1-yl]propyl}-2,3-dihydro-1H-indole, Hydrochloride Lithium aluminium hydride (1.8 g) was suspended in tetrahydrofuran (30 mL) at 0° C., and the suspension was added a solution of aluminium trichloride (1.8 g) in tetrahydrofuran (30 mL) at 0–5° C. over 15 min. To this mixture, a solution of 1a, 3-[4-(2,3-dichlorophenyl)piperazin-1-yl]-1-(2,3-dihydro-1H-indol-1-yl)propan-1-one (5 g) in tetrahydrofuran (50 mL) was added at a temperature of 0–10° C. The resulting mixture was stirred for 30 min at 5° C. and then for 2 h at room temperature. The reaction mixture was quenched with water and sodium hydroxide (28%) and filtered. The organic phase was evaporated to dryness in vacuo, and the title compound was precipitated as the hydrochloride salt and recrystallised from ethanol (3.8 g). Mp 214–226° C. $^1$H NMR (DMSO-d$_6$): 2.05–2.20 (m, 2H); 2.95 (t, 2H); 3.10–3.35 (m, 8H); 3.35–3.50 (m, 4H); 3.60 (d, 2H); 6.70 (b s, 2H); 7.05 (t, 1H); 7.10 (d, 1H); 7.20 (d, 1H); 7.30–7.40 (m, 2H); 11.45 (b s). MS m/z: 390 (MH+), 271, 132.

The following compounds were prepared in a similar manner 2b, 1-{4-[4-(2,3-Dichlorophenyl)piperazin-1-yl]butyl}-2,3-dihydro-1H-indole, oxalate from 1b, 4-[4-(2,3-dichlorophenyl)piperazin-1-yl]-1-(2,3-dihydro-1H-indol-1-yl)butan-1-one. Mp 157–160° C. $^1$H NMR (DMSO-d$_6$): 1.55–1.65 (m, 2H); 1.65–1.75 (m, 2H); 2.90 (t, 2H); 2.95 (t, 2H); 3.05 (t, 2H); 3.05–3.25 (m, 8H); 3.30 (t, 2H); 6.50 (d, 1H); 6.55 (t, 1H); 6.95 (t, 1H); 7.00 (d, 1H); 7.20 (d, 1H); 7.30–7.40 (m, 2H). MS m/z: 404 (MH+), 285, 174, 132.

2c, 1-{5-[4-(2,3-Dichlorophenyl)piperazin-1-yl]pentyl}-2,3-dihydro-1H-indole, hydrochloride from 1c, 5-[4-(2,3-dichlorophenyl)piperazin-1-yl]-1-(2,3-dihydro-1H-indol-1-yl)pentan-1-one. Mp 219–228° C. $^1$H NMR (DMSO-d$_6$): 1.35–1.45 (m, 2H); 1.60–1.70 (m, 2H); 1.80–1.90 (m, 2H); 2.95–3.05 (m, 2H); 3.10–3.30 (m, 8H); 3.40–3.65 (m, 6H); 6.85 (b s, 2H); 7.05–7.25 (m, 3H); 7.30–7.40 (m, 2H); 11.20 (b s). MS m/z: 418 (MH+), 299, 188.

2d, 1-{4-[4-(2-Chlorophenyl)piperazin-1-yl]butyl}-2,3-dihydro-1H-indole, oxalate from 1d, 4-[4-(2-chlorophenyl)piperazin-1-yl]-1-(2,3-dihydro-1H-indol-1-yl)butan-1-one. Mp 146–148° C. $^1$H NMR (DMSO-d$_6$): 1.55–1.60 (m, 2H); 1.65–1.75 (m, 2H); 2.90 (t, 2H); 3.00 (t, 2H); 3.05 (t, 2H); 3.15 (b s, 8H); 3.30 (t, 2H); 6.50 (d, 1H); 6.55 (t, 1H); 7.00 (t, 1H); 7.05 (d, 1H); 7.10 (t, 1H); 7.20 (d, 1H); 7.35 (t, 1H); 7.45 (d, 1H). MS m/z: 370 (MH+), 251, 174.

2e, 1-{4-[4-(3-Chlorophenyl)piperazin-1-yl]butyl}-2,3-dihydro-1H-indole, oxalate from 1e, 4-[4-(3-chlorophenyl)piperazin-1-yl]-1-(2,3-dihydro-1H-indol-1-yl)butan-1-one. Mp 172–176° C. $^1$H NMR (DMSO-d$_6$): 1.55–1.60 (m, 2H); 1.65–1.75 (m, 2H); 2.85 (t, 2H); 2.95 (t, 2H); 3.00–3.20 (m, 6H); 3.30 (t, 2H); 3.40 (b s, 4H); 6.50 (d, 1H); 6.55 (t, 1H); 6.85 (d, 1H); 6.90–7.05 (m, 4H); 7.25 (t, 1H). MS m/z: 370 (MH+), 251, 174.

EXAMPLE 3

3, 1-(2,3-Dichlorophenyl)-4-[4-(indan-1-yl)butyl]piperazine, oxalate

A mixture of 1-(2,3-dichlorophenyl)piperazine, hydrochloride (3.5 g) and diisopropylethylamine in a mixture of methyl isobutyl ketone (50 mL) and dimethyl formamide (5 mL) was heated to 60° C. followed by the addition of 4-(indan-1-yl)butyl methanesulfonate (3.5 g) in methyl isobutyl ketone (10 mL). The resulting mixture was boiled under reflux for 5 h and reduced in vacuo. The product was purified by flash chromatography on silicagel (eluent ethylacetate) to give the crude product that subsequently was precipitated as the oxalate salt (0.7 g). Mp 171–176° C. $^1$H NMR (DMSO-d$_6$): 1.35–1.45 (m, 3H); 1.55–1.75 (m, 3H); 1.80–1.90 (m, 1H); 2.20–2.30 (m, 2H); 2.75–2.90 (m, 2H); 2.95 (t, 1H); 3.10 (t, 1H); 3.20 (b s, 8H); 7.10–7.15 (m, 2H); 7.15–7.25 (m, 3H); 7.30–7.40 (m, 2H). MS m/z: 403 (MH+).

EXAMPLE 4

4, 6-Chloro-3-{2-[4-(2,3-dichlorophenyl)piperazin-1-yl] ethylsulfanyl}-1H-indole, oxalate A solution of (6-chloro-1H-indol-3-ylsulfanyl)acetic acid (1.75 g) in tetrahydrofuran (30 mL) was added carbonyldiimidazole (1.2 g), stirred at room temperature for 30 min and cooled to 5° C. To this mixture was added 1-(2,3-dichlorophenyl)piperazine (1.8 g) dissolved in tetrahydrofuran (20 mL), and the resulting mixture was stirred at room temperature for 2 h. The mixture was poured into water, and the aqueous phase was extracted with ethyl acetate. The combined organic phase was dried (MgSO$_4$), filtered and evaporated in vacuo to give an oil (3.6 g). The oil was subjected to the same reaction conditions (reduction with alane) as described in example 2, and the product was purified by flash chromatography on silicagel (eluent:ethylacetate/heptane 5:1) to give an oil. The title compound was isolated as the oxalate salt (0.8 g). Mp 137–141° C. $^1$H NMR (DMSO-d$_6$): 2.75–2.95 (m, 8H); 2.95–3.15 (m, 4H); 7.10–7.20 (m, 2H); 7.25–7.35 (m, 2H); 7.50 (s, 1H); 7.60–7.70 (m, 2H). 11.60 (b s, 1H). MS m/z: 442 (MH+), 291, 182.

EXAMPLE 5

5a, 3-{3-[4-(2,3-Dichlorophenyl)piperazin-1-yl]propyl}-1H-indole, hydrochloride

A mixture of 3-(3-bromopropyl)-1H-indole (1.19 g), potassium carbonate (1.4 g) and 1-(2,3-dichlorophenyl)piperazine (1.27 g) in anhydrous acetonitrile (10 mL) was boiled under reflux for 5 h and cooled to room temperature. The mixture was added silicagel (7 g), and the solvent was evaporated in vacuo. The compound was purified by flash chromatography on silicagel (eluent:ethylacetate/heptane/triethylamine 49:49:2). Fractions containing the compound were combined and evaporated in vacuo. Recrystallisation from acetonitrile gave the title compound as a white crystalline material. The compound was precipitated as the hydrochloride salt (1 g). Mp 241–242° C. $^1$H NMR (DMSO-d$_6$): 2.10–2,5 (m, 2H); 2.75 (t, 2H); 3.10–3.30 (m, 6H); 3.40 (t, 2H); 3.60 (d, 2H); 7.00 (t, 1H); 7.05 (t, 1H); 7.15 (d, 1H); 7.25 (s, 1H); 7.30–7.40 (m, 3H); 7.55 (d, 1H); 10.90 (b s, 1H); 11.40 (b s, 1H). Ms m/z: 388 (MH+).

The following compounds were prepared in a similar manner 5b, 3-{4-[4-(2,3-Dichlorophenyl)piperazin-1-yl]butyl}-1H-indole, hydrochloride from 1-(2,3-dichlorophenyl)piperazine and 3-(4-bromobutyl)-1H-indole. Mp 121–122° C. $^1$H NMR (DMSO-d$_6$): 1.45–1.55 (m, 2H); 1.65–1.75 (m, 2H); 2.35 (t, 2H); 2.50 (b s, 4H); 2.70 (t, 2H); 2.95 (b s, 4H); 6.95 (t, 1H); 7.05 (t, 1H); 7.10–7.15 (m, 2H); 7.25–7.30 (m, 2H); 7.35 (d, 1H); 7.50 (d, 1H); 10.75 (b s, 1H). Ms m/z: 402 (MH+).

5c, 3-{3-[4-(2,3-Dichlorophenyl)piperazin-1-yl]propyl}-5-fluoro-1H-indole from 1-(2,3-dichlorophenyl)piperazine and 3-(3-chloropropyl)-5-fluoro-1H-indole. Mp 147–148° C. $^1$H NMR (DMSO-d$_6$): 1.75–1.85 (m, 2H); 2.30–2.45 (t, 2H); 2.45–2.60 (m, 2H); 2.70 (t, 2H); 3.00 (b s, 4H); 3.35 (b s, 2H); 6.85–6.95 (m, 1H); 7.05–7.15 (m, 1H); 7.20 (s, 1H); 7.20–7.35 (m, 4H); 10.85 (b s, 1H). Ms m/z: 406 (MH+).

5d, 3-{4-[4-(2,3-Dichlorophenyl)piperazin-1-yl]butyl}-5-fluoro-1H-indole from 1-(2,3-dichlorophenyl)piperazine and 3-(4-chlorobutyl)-5-fluoro-1H-indole. Mp 147–148° C. $^1$H NMR (DMSO-d$_6$): 1.45–1.55 (m, 2H); 1.60–1.70 (m, 2H); 2.35 (t, 2H); 2.50 (b s, 4H); 2.65 (t, 2H); 2.95 (b s, 4H); 6.85–6.95 (m, 1H); 7.10–7.15 (m, 1H); 7.20 (s, 1H); 7.25–7.35 (m, 4H); 10.85 (b s, 1H). Ms m/z: 420 (MH+).

5e, 6-Chloro-3-{3-[4-(2,3-dichlorophenyl)piperazin-1-yl] propyl}-1H-indole from 1-(2,3-dichlorophenyl)piperazine and 6-chloro 3-(3-iodopropyl)-1H-indole. $^1$H NMR (CDCl$_3$): 1.95 (t, 2H); 2.55 (t, 2H); 2.65 (b s, 4H); 2.80 (t, 2H); 3.10 (b s, 4H); 6.95–7.05 (m, 2H); 7.10 (d, 1H); 7.10–7.20 (m, 2H); 7.35 (s, 1H); 7.55 (d, 1H); 7.95 (b s, 1H). Ms m/z: 422 (MH+), 424.

EXAMPLE 6

6, 1-{4-[4-(2,3-Dichlorophenyl)piperazin-1-yl]butyl}-3,4-dihydroquinolin-2(1H)-one The free base of 1-(2,3-dichlorophenyl)piperazine, hydrochloride (6.0 g) was liberated by the use ethyl acetate and aqueous ammonia. The remaining oil was dissolved in butanone (500 mL) followed by the addition of potassium carbonate (9.7 g), and the mixture was heated to reflux temperature. To this mixture was added a solution of 1-(4-bromobutyl)-3,4-dihydroquinolin-2(1H)-one (7.9 g) in butanone (150 mL), and the resulting mixture was boiled under reflux for 10 h. The mixture was filtered hot and purified by flash chromatography (eluent:ethyl acetate/triethylamine 100:4) giving the title compound which was precipitated as the hydrochloride salt (2.5 g). Mp 234–235° C. $^1$H NMR (DMSO-d$_6$): 1.55–1.65 (m, 2H); 1.75–1.85 (m, 2H); 2.55 (t, 2H); 2.85–2.90 (m, 2H); 3.05–3.20 (m, 4H); 3.25 (t, 2H); 3.40 (d, 2H); 3.55 (d, 2H); 3.95 (t, 2H); 7.00 (t, 1H); 7.15 (d, 1H); 7.20–7.30 (m, 3H); 7.30–7.40 (m, 2H); 11.35 (b s). MS m/z: 432 (MH+).

EXAMPLE 7

7a, 3-[4-(2,3-Dichlorophenyl)piperazin-1-yl]-1-(5-fluoro-2,3-dihydro-1H-indol-1-yl)propan-1-one 3-Bromopropanoyl chloride (1 g in 10 ml dry dichloromethane) was added with stirring at 0° C. to a suspension of 1 g Wang resin (Rapp polymere, loading 0.95 mmol/g) in 10 ml dry dichloromethane containing 5 equivalents of diisopropylethyl amine. The mixture was stirred overnight at room temperature, filtered and washed with dry dichloromethane (6×100 ml). A solution of 1-(2,3-dichlorophenyl) piperazine (2.5 equivalents) in dry acetonitrile containing diisopropylethyl amine (5 equivalents) was added to the dried resin and the mixture heated to 70° C. for 3 hours. The mixture was cooled to room temperature and the resin washed with dry acetonitrile and dichloromethane and dried. A solution of AlCl$_3$ (1.1 equivalent) in dry acetonitrile (5 ml) was added to the resin followed by a solution of 5-fluoro-2,3-dihydro-1H-indole (3 equivalents) in dry acetonitrile (5 ml) and the mixture agitated for 3 hours. The reaction was quenched by addition of 2N NaOH (1.2 equivalent), filtrated and the product purified by solid phase ion exchange chromatography (Varian SCX columns) using Gilson ASPEC 232 XL. Further purification was performed on a PE Sciex API 150EX instrument equipped with IonSpray source and Shimadzu LC-8A/SLC-10A LC system. The LC conditions (50×20 mm YMC ODS-A with 5 μm particle size) were linear gradient elution with water/acetonitrile/trifluoroacetic acid (80:20:0.05) to water/acetonitrile/trifluoroacetic acid (10:90:0.03) in 7 min at 22.7 mL/min. Fraction collection was performed by split-flow MS detection. Purity was determined by integration of the UV trace (254 nm). The retention times RT are expressed in minutes. LC/MS (m/z) 422 (MH+), RT=2.49, purity: 70.57%

The following compounds were prepared in a similar manner 7b, 4-[4-(2,3-Dichlorophenyl)piperazin-1-yl]-1-(5-fluoro-2,3-dihydro-1H-indol-1-yl)butan-1-one: LC/MS (m/z) 436 (MH+), RT=2.58, purity: 96.23%

7c, 5-[4-(2,3-Dichlorophenyl)piperazin-1-yl]-1-(5-fluoro-2,3-dihydro-1H-indol-1-yl)pentan-1-one: LC/MS (m/z) 450 (MH+), RT=2.56, purity: 81.68%

7d, 3-[4-(2,3-Dichlorophenyl)piperazin-1-yl]-1-(3,4-dihydro-1H-isoquinolin-2-yl)-propan-1-one: LC/MS (m/z) 418 (MH+), RT=2.43, purity: 72.99%

7e, 4-[4-(2,3-Dichlorophenyl)piperazin-1-yl]-1-(3,4-dihydro-1H-isoquinolin-2-yl)-pentan-1-one: LC/MS (m/z) 432 (MH+), RT=2.49, purity: 81.86%

7f, 5-[4-(2,3-Dichloro-phenyl)-piperazin-1-yl]-1-(3,4-dihydro-1H-isoquinolin-2-yl)propan-1-one: LC/MS (m/z) 446 (MH+), RT=2.49, purity: 98.39%

8a, 3-[4-(2-Chlorophenyl)piperazin-1-yl]-1-(2,3-dihydro-1H-indol-1-yl)propan-1-one: LC/MS (m/z) 370 (MH+), RT=2.29, purity: 92.49%

8b, 5-[4-(2-Chlorophenyl)piperazin-1-yl]-1-(2,3-dihydro-1H-indol-1-yl)pentan-1-one: LC/MS (m/z) 398 (MH+), RT=2.37, purity: 70.1%

8c, 3-[4-(3-Chlorophenyl)piperazin-1-yl]-1-(2,3-dihydro-1H-indol-1-yl)propan-1-one: LC/MS (m/z) 370 (MH+), RT 2.33, purity: 81.15%

8d, 5-[4-(3-Chlorophenyl)piperazin-1-yl]-1-(2,3-dihydro-1H-indol-1-yl)pentan-1-one: LC/MS (m/z) 398 (MH+), RT=2.41, purity: 96.58%

8e, 3-[4-(3-Chlorophenyl)piperazin-1-yl]-1-(5-fluoro-2,3-dihydro-1H-indol-1-yl)pentan-1-one: LC/MS (m/z) 388 (MH+), RT=2.37, purity: 92.8%

8f, 5-[4-(3-Chlorophenyl)piperazin-1-yl]-1-(5-fluoro-2,3-dihydro-1H-indol-1-yl)propan-1-one: LC/MS (m/z) 416 (MH+), RT=2.45, purity: 96.43%

8g, 3-[4-(2-Chlorophenyl)piperazin-1-yl]-1-(5-fluoro-2,3-dihydro-1H-indol-1-yl)pentan-1-one: LC/MS (m/z) 388 (MH+), RT=2.33, purity: 93.11%

8h, 4-[4-(2-Chlorophenyl)piperazin-1-yl]-1-(5-fluoro-2,3-dihydro-1H-indol-1-yl)butan-1-one: LC/MS (m/z) 402 (MH+), RT=2.43, purity: 89.76%

8i, 3-[4-(3-Chlorophenyl)piperazin-1-yl]-1-(3,4-dihydro-1H-isoquinolin-2-yl)-propan-1-one: LC/MS (m/z) 384 (MH+), RT=2.31, purity: 92.21%

8j, 5-[4-(3-Chlorophenyl)piperazin-1-yl]-1-(3,4-dihydro-1H-isoquinolin-2-yl)-pentan-1-one: LC/MS (m/z) 412 (MH+), RT=2.37, purity: 95.37%

8k, 3-[4-(2-Chlorophenyl)piperazin-1-yl]-1-(3,4-dihydro-1H-isoquinolin-2-yl)-propan-1-one: LC/MS (m/z) 384 (MH+), RT=2.27, purity: 91.51%

8l, 4-[4-(2-Chlorophenyl)piperazin-1-yl]-1-(3,4-dihydro-1H-isoquinolin-2-yl)-butan-1-one: LC/MS (m/z) 398 (MH+), RT=2.35, purity: 97.56%

9a, 1-(2,3-Dihydro-1H-indol-1-yl)-3-[4-(2-fluoro-phenyl)-piperazin-1-yl]-propan-1-one: LC/MS (m/z) 354 (MH+), RT=2.14, purity: 91.64%

9b, 1-(2,3-Dihydro-1H-indol-1-yl)-4-[4-(2-fluoro-phenyl)-piperazin-1-yl]-butan-1-one: LC/MS (m/z) 368 (MH+), RT=2.24, purity: 76.25%

9c, 1-(2,3-Dihydro-1H-indol-1-yl)-5-[4-(2-fluoro-phenyl)-piperazin-1-yl]-pentan-1-one: LC/MS (m/z) 382 (MH+), RT=2.22, purity: 87.9%

9d, 1-(5-Fluoro-2,3-dihydro-1H-indol-1-yl)-3-[4-(2-fluoro-phenyl)-piperazin-1-yl]-propan-1-one: LC/MS (m/z) 372 (MH+), RT=2.22, purity: 76.87%

9e, 1-(5-Fluoro-2,3-dihydro-1H-indol-1-yl)-4-[4-(2-fluoro-phenyl)-piperazin-1-yl]-butan-1-one: LC/MS (m/z) 386 (MH+), RT=2.31, purity: 86.01%

9f, 1-(5-Fluoro-2,3-dihydro-1H-indol-1-yl)-5-[4-(2-fluoro-phenyl)-piperazin-1-yl]-pentan-1-one: LC/MS (m/z) 400 (MH+), RT=2.31, purity: 97.52%

9g, 3-[4-(2,4-Difluoro-phenyl)-piperazin-1-yl]-1-(2,3-dihydro-1H-indolyl)propan-1-yl)propan-1-one: LC/MS (m/z) 372 (MH+), RT=2.2, purity: 94.79%

9h, 4-[4-(2,4-Difluoro-phenyl)-piperazin-1-yl]-1-(2,3-dihydro-1H-indol-1-yl)butan-1-one: LC/MS (m/z) 386 (MH+), RT=2.29, purity: 79.75%

9i, 5-[4-(2,4-Difluoro-phenyl)-piperazin-1-yl]-1-(2,3-dihydro-1H-indol-1-yl)pentan-1-one: LC/MS (m/z) 400 (MH+), RT=2.29, purity: 99.06%

9j, 3-[4-(2,4-Difluoro-phenyl)-piperazin-1-yl]-1-(5-fluoro-2,3-dihydro-1H-indol-1-yl)propan-1-one: LC/MS (m/z) 390 (MH+), RT=2.27, purity: 87.99%

9k, 1-(3,4-Dihydro-1H-isoquinolin-2-yl)-4-[4-(2-fluoro-phenyl)-piperazin-1-yl]-butan-1-one: LC/MS (m/z) 382 (MH+), RT=2.22, purity: 87.75%

9l, 1-(3,4-Dihydro-1H-isoquinolin-2-yl)-5-[4-(2-fluoro-phenyl)-piperazin-1-yl]-pentan-1-one: LC/MS (m/z) 396 (MH+), RT=2.22, purity: 85.52%

9m, 3-[4-(2,4-Difluoro-phenyl)-piperazin-1-yl]-1-(3,4-dihydro-1H-isoquinolin-2-yl)-propan-1-one: LC/MS (m/z) 385 (MH+), RT=2.22, purity: 87.01%

9n, 5-[4-(2,4-Difluoro-phenyl)-piperazin-1-yl]-1-(3,4-dihydro-1H-isoquinolin-2-yl)-pentan-1-one: LC/MS (m/z) 414 (MH+), RT=2.31, purity: 87.84%

10a, 3-[4-(3,4-Dichlorophenyl)piperazin-1-yl]-1-(2,3-dihydro-1H-indol-1-yl)propan-1-one: LC/MS (m/z) 404 (MH+), RT=2.47, purity: 76.03%

10b, 4-[4-(3,4-Dichlorophenyl)piperazin-1-yl]-1-(2,3-dihydro-1H-indol-1-yl)butan-1-one: LC/MS (m/z) 418 (MH+), RT=2.58, purity: 99.32%

10c, 3-[4-(3,4-Dichlorophenyl)piperazin-1-yl]-1-(5-fluoro-2,3-dihydro-1H-indol-1-yl)propan-1-one: LC/MS (m/z) 422 (MH+), RT=2.52, purity: 80.99%

10d, 3-[4-(3,4-Dichlorophenyl)piperazin-1-yl]-1-(3,4-dihydro-1H-isoquinolin-2-yl)-propan-1-one: LC/MS (m/z) 418 (MH+), RT=2.45, purity: 83.31%

10e, 5-[4-(3,4-Dichlorophenyl)piperazin-1-yl]-1-(3,4-dihydro-1H-isoquinolin-2-yl)-pentan-1-one: LC/MS (m/z) 446.1 (MH+), RT=2.52, purity: 98.79%

Pharmacological Testing

The compounds of the invention were tested by the use of well-recognised and reliable methods. The tests were as follows:

Inhibition of the Binding of [$^3$H]YM-09151-2 to Human Dopamine $D_4$ Receptors By this method the inhibition by drugs of the binding of [$^3$H]YM-09151-2 (0.06 nM) to membranes of human cloned dopamine $D_{4.2}$ receptors expressed in CHO-cells is determined in vitro. Method modified from NEN Life Science Products, Inc., technical data certificate PC2533-10/96. The results are given in the following Table I as $IC_{50}$-values.

Inhibition of the Binding of [$^3$H]Spiperone to Human $D_3$ Receptors

By this method the inhibition by drugs of the binding [$^3$H]Spiperone (0.3 nM) to membranes of human cloned dopamine $D_3$ receptors expressed in CHO-cells is determined in vitro. Method modified from MacKenzie et al. *Eur. J. Pharm.-Mol. Pharm. Sec.* 1994, 266, 79–85. The results are given in the following Table 1.

Inhibition of Binding of [$^3$H]Prazosine to Rat Alpha-1 Receptors

By this method the inhibition by drugs of the binding of [$^3$H]Prazosine (0.25 nM) to alpha-1 receptors in membranes from rat brain is determined in vitro. Method modified from Hyttel et al. *J. Neurochem.* 1985, 44, 1615–1622. The results are given in the following Table 1.

TABLE 1

Binding Data ($IC_{50}$ values in nM or as % inhibition of binding at 100 nM)

| Comp. No. | $D_4$-bind. | $D_3$-bind. | Alpha-1 |
| --- | --- | --- | --- |
| 1a | 3.3 | 100 | 59 |
| 1b | 2.8 | 3.0 | 1100 |
| 1c | 39 | 10 | 160 |
| 1d | 0.92 | 20 | 97 |
| 1e | 2.1 | 50 | 17 |
| 2a | 1.8 | 31 | 68 |
| 2b | 12 | 3.1 | 10% |
| 2c | 18 | 22 | 190 |
| 2d | 1.2 | 4.0 | 31 |
| 2e | 1.6 | 17 | 40 |
| 3 | 11 | 6.8 | −3% |
| 4 | 500 | 40 | 4800 |
| 5a | 2.2 | 2.8 | 410 |
| 5b | 14 | 1.1 | 570 |
| 5c | 3.9 | 6.8 | 960 |
| 5d | 8.6 | 1.0 | 720 |
| 5e | 27 | 93% | 470 |
| 6 | 16 | 1.8 | 43 |
| 7a | 25 | 73% | 38% |
| 7b | 53 | 65% | 6% |
| 7c | 61 | 92% | 45% |
| 7d | 6.0 | 85% | 44% |
| 7e | 10 | 94% | 31% |
| 7f | 26 | 95% | 34% |
| 8k | 8.0 | 73% | 92% |
| 8l | 4.0 | 88% | 74% |
| 9k | 9.0 | 92% | 69% |

The compounds were also tested in the following test:

Inhibition of the Binding of [$^3$H]Spiroperidol to $D_2$ Receptors

The compounds were tested with respect to affinity for the dopamine $D_2$ receptor by determining their ability to inhibit the binding of [$^3$H]-spiroperidol to $D_2$ receptors by the method of Hyttel et al. *J. Neuroche.* 1985, 44, 1615.

In general, the compounds of the invention have been found to have high affinity for dopamine $D_4$ receptors and dopamine $D_3$ receptors. The compounds have only weak or no affinity for the dopamine $D_2$ receptor.

One important effects of adrenergic alpha-1-receptor blockade is postural hypotension resulting from a fall in central venous pressure due to dilation of small capacitance vessels. This effect may further be accompanied by a decrease in cardiac output. Certain compounds of the invention have the further advantage of having only very weak effect at adrenergic alpha-1-receptors which imply a low propensity to cause orthostatic hypotension.

Certain of the compounds interact with central serotonergic receptors, such as the $5-HT_{1A}$ and/or the $5-HT_{2A}$ receptors and/or they act as 5-HT reuptake inhibitors.

Accordingly, the compounds of the invention are considered useful in the treatment of psychosis including the positive and negative symptoms of schizophrenia, affective disorders such as generalised anxiety disorder, panic disorder, and obsessive compulsive disorder, depression, aggression cognitive disorders and dyskinesia induced by treatment with L-dopa comprising.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients or other additives normally used in the art may be used.

Conveniently, the compounds of the invention are administered in unit dosage form containing said compounds in an amount of about 0.01 to 100 mg.

The total daily dose is usually in the range of about 0.05–500 mg, and most preferably about 0.1 to 50 mg of the active compound of the invention.

FORMULATION EXAMPLES

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilisation of the solution and filling in suitable ampules or vials. Any suitable additive conventionally used in the art may be added, such as tonicity agents, preservatives, antioxidants, etc.

Typical examples of recipes for the formulation of the invention are as follows:

1) Tablets containing 5.0 mg of active compound calculated as the free base:

| Compound of formula I | 5.0 mg |
|---|---|
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of active compound calculated as the free base:

| Compound of formula I | 0.5 mg |
|---|---|
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup containing per milliliter:

| Compound of formula i | 25 mg |
|---|---|
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 ml |
| Flavour | 0.05 mg |
| Saccharin sodium | 0.5 mg |
| Water | ad 1 ml |

4) Solution for injection containing per milliliter:

| Compound of formula I | 0.5 mg |
|---|---|
| Sorbitol | 5.1 mg |
| Acetic Acid | 0.05 mg |
| Saccharin sodium | 0.5 mg |
| Water | ad 1 ml |

What is claimed is:

1. A compound of formula I

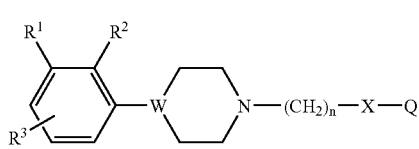

wherein
W is N;
$R^1$ and $R^2$ are independently halogen;
$R^3$ is selected from hydrogen, halogen, $C_{1-6}$-alkyl, $C_{2-6}$-alkenyl, $C_{2-6}$-alkynyl, trifluoromethyl, $C_{1-6}$-alkoxy, aryloxy, aralkoxy, hydroxy, amino, $C_{1-6}$-alkylamino, di($C_{1-6}$-alkyl)amino, nitro and cyano;
n is 2, 3, 4 or 5;
X is $CH_2$, O, CO, CS, SO or $SO_2$; and
Q is a group of formula

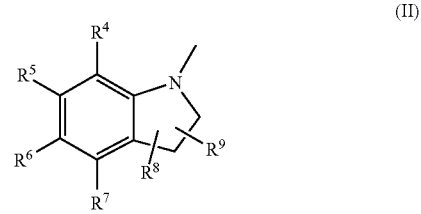

wherein $R^4$, $R^5$, $R^6$, $R^7$, $R^8$ and $R^9$ are independently selected from hydrogen, halogen, trifluoromethyl, nitro, cyano, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, hydroxy, hydroxy-$C_{1-6}$ alkyl, amino, $C_{1-6}$-alkylamino, di($C_{1-6}$-alkyl)amino, aminocarbonyl, $C_{1-6}$-alkylaminocarbonyl and di($C_{1-6}$-alkyl)aminocarbonyl;
and any of its enantiomers and acid addition salts thereof.

2. A compound according to claim 1 wherein $R^1$ and $R^2$ are both chloro.

3. A compound according to claim 1 wherein X is CO or $CH_2$.

4. A compound according to claim 3 wherein Q is unsubstituted or substituted with halogen.

5. A compound according to claim 1 wherein $R^3$ is hydrogen or $R^3$ is attached in the para position on the phenyl ring.

6. A compound according to claim 5 wherein $R^3$ is halogen.

7. A pharmaceutical composition comprising a compound of claim 1 in a therapeutically effective amount together with one or more pharmaceutically acceptable carriers or diluents.

8. A method of treating affective disorders, psychosis, depression, aggression, and dyskinesia induced by treatment with L-dopa, comprising administration of a therapeutically acceptable amount of a compound of claim 1 to a patient in need thereof.

9. The method of claim 8, wherein the psychosis is the positive and negative symptoms of schizophrenia.

10. The method of claim 8, wherein the affective disorders are selected from the group consisting of generalised anxiety disorder, panic disorder, and obsessive compulsive disorder.

11. A compound of formula I

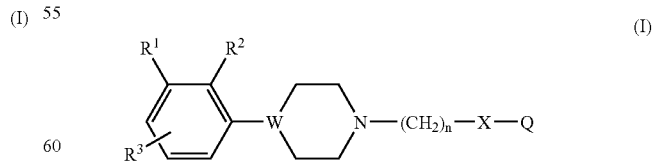

wherein
W is N;
$R^1$ and $R^2$ are independently selected from hydrogen and halogen, provided at least one of $R^1$ and $R^2$ is a halogen atom;

$R^3$ is selected from hydrogen, halogen, $C_{1-6}$-alkyl, $C_{2-6}$-alkenyl, $C_{2-6}$-alkynyl, trifluoromethyl, $C_{1-6}$-alkoxy, aryloxy, aralkoxy, hydroxy, amino, $C_{1-6}$-alkylamino, di($C_{1-6}$-alkyl)amino, nitro and cyano;

n is 2, 3, 4 or 5;

X is CS, SO or $SO_2$; and

Q is a group of formula

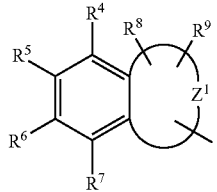
(II)

wherein Z is a 3-membered nitrogen-containing chain wherein the chain members are selected from C, CH, $CH_2$, CO, N and NH, provided that only one of the chain members may be N or NH, and said chain Z optionally containing one double bond;

$R^4$, $R^5$, $R^6$, $R^7$, $R^8$ and $R^9$ are independently selected from hydrogen, halogen, trifluoromethyl, nitro, cyano, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, hydroxy, hydroxy-$C_{1-6}$ alkyl, amino, $C_{1-6}$-alkylamino, di($C_{1-6}$-alkyl)amino, aminocarbonyl, $C_{1-6}$-alkylaminocarbonyl and di($C_{1-6}$-alkyl)aminocarbonyl;

and any of its enantiomers and acid addition salts thereof.

12. A compound according to claim 11 wherein $R^1$ and $R^2$ are both halogen.

13. A compound according to claim 11 wherein $R^1$ and $R^2$ are both chloro.

14. A compound according to claim 11 wherein one of $R^1$ and $R^2$ is halogen and the other is hydrogen.

15. A compound according to claim 14 wherein $R^2$ is halogen.

16. A compound according to claim 14 wherein $R^1$ is halogen.

17. A compound according to claim 11 wherein $R^1$ and $R^2$ are independently selected from hydrogen or chloro.

18. A compound according to claim 11 wherein Z is a 3-membered nitrogen-containing chain, wherein the chain members are selected from C, CH, $CH_2$, N and NH, provided that only one of the chain members may be N or NH.

19. A method of treating affective disorders, psychosis, depression, aggression, and dyskinesia induced by treatment with L-dopa, comprising administration of a therapeutically acceptable amount of a compound of claim 11 to a patient in need thereof.

20. The method of claim 19, wherein the psychosis is the positive and negative symptoms of schizophrenia.

21. The method of claim 19, wherein the affective disorders are selected from the group consisting of generalised anxiety disorder, panic disorder, and obsessive compulsive disorder.

22. The compound of claim 1 wherein the compound is
3-[4-(2,3-dichlorophenyl)piperazin-1-yl]-1-(2,3-dihydro-1H-indol-1-yl)propan-1-one;
4-[4-(2,3-dichlorophenyl)piperazin-1-yl]-1-(2,3-dihydro-1H-indol-1-yl)butan-1-one;
5-[4-(2,3-dichlorophenyl)piperazin-1-yl]-1-(2,3-dihydro-1H-indol-1-yl)pentan-1-one;
1-{3-[4-(2,3-dichlorophenyl)piperazin-1-yl]propyl}-2,3-dihydro-1H-indole;
1-{4-[4-(2,3-dichlorophenyl)piperazin-1-yl]butyl}-2,3-dihydro-1H-indole;
1-{5-[4-(2,3-dichlorophenyl)piperazin-1-yl]pentyl}-2,3-dihydro-1H-indole;
3-[4-(2,3-dichlorophenyl)piperazin-1-yl]-1-(5-fluoro-2,3-dihydro-1H-indol-1-yl)propan-1-one;
4-[4-(2,3-dichlorophenyl)piperazin-1-yl]-1-(5-fluoro-2,3-dihydro-1H-indol-1-yl)butan-1-one;
5-[4-(2,3-dichlorophenyl)piperazin-1-yl]-1-(5-fluoro-2,3-dihydro-1H-indol-1-yl)pentan-1-one; or any enantiomer or acid addition salt thereof.

23. The pharmaceutical composition of claim 7 which comprises the compound
3-[4-(2,3-dichlorophenyl)piperazin-1-yl]-1-(2,3-dihydro-1H-indol-1-yl)propan-1-one;
4-[4-(2,3-dichlorophenyl)piperazin-1-yl]-1-(2,3-dihydro-1H-indol-1-yl)butan-1-one;
5-[4-(2,3-dichlorophenyl)piperazin-1-yl]-1-(2,3-dihydro-1H-indol-1-yl)pentan-1-one;
1-{3-[4-(2,3-dichlorophenyl)piperazin-1-yl]propyl}-2,3-dihydro-1H-indole;
1-{4-[4-(2,3-dichlorophenyl)piperazin-1-yl]butyl}-2,3-dihydro-1H-indole;
1-{5-[4-(2,3-dichlorophenyl)piperazin-1-yl]pentyl}-2,3-dihydro-1H-indole;
3-[4-(2,3-dichlorophenyl)piperazin-1-yl]-1-(5-fluoro-2,3-dihydro-1H-indol-1-yl)propan-1-one;
4-[4-(2,3-dichlorophenyl)piperazin-1-yl]-1-(5-fluoro-2,3-dihydro-1H-indol-1-yl)butan-1-one;
5-[4-(2,3-dichlorophenyl)piperazin-1-yl]-1-(5-fluoro-2,3-dihydro-1H-indol-1-yl)pentan-1-one; or any enantiomer or acid addition salt thereof.

24. The method of claim 8 wherein the administered compound is
3-[4-(2,3-dichlorophenyl)piperazin-1-yl]-1-(2,3-dihydro-1H-indol-1-yl)propan-1-one;
4-[4-(2,3-dichlorophenyl)piperazin-1-yl]-1-(2,3-dihydro-1H-indol-1-yl)butan-1-one;
5-[4-(2,3-dichlorophenyl)piperazin-1-yl]-1-(2,3-dihydro-1H-indol-1-yl)pentan-1-one;
1-{3-[4-(2,3-dichlorophenyl)piperazin-1-yl]propyl}-2,3-dihydro-1H-indole;
1-{4-[4-(2,3-dichlorophenyl)piperazin-1-yl]butyl}-2,3-dihydro-1H-indole;
1-{5-[4-(2,3-dichlorophenyl)piperazin-1-yl]pentyl}-2,3-dihydro-1H-indole;
3-[4-(2,3-dichlorophenyl)piperazin-1-yl]-1-(5-fluoro-2,3-dihydro-1H-indol-1-yl)propan-1-one;
4-[4-(2,3-dichlorophenyl)piperazin-1-yl]-1-(5-fluoro-2,3-dihydro-1H-indol-1-yl)butan-1-one;
5-[4-(2,3-dichlorophenyl)piperazin-1-yl]-1-(5-fluoro-2,3-dihydro-1H-indol-1-yl)pentan-1-one; or any enantiomer or acid addition salt thereof.

* * * * *